US006156938A

United States Patent [19]
Sobolev et al.

[11] Patent Number: 6,156,938
[45] Date of Patent: Dec. 5, 2000

[54] PROCESS FOR MAKING PHENOL OR PHENOL DERIVATIVES

[75] Inventors: Vladimir I. Sobolev, Novosibirsk, Russian Federation; Mikhail A. Rodkin, Pace; Anthony K. Uriarte, Pensacola, both of Fla.; Gennady I. Panov, Novosibirsk, Russian Federation

[73] Assignee: Solutia, Inc., St. Louis, Mo.

[21] Appl. No.: 09/052,256

[22] Filed: Mar. 31, 1998

Related U.S. Application Data

[60] Provisional application No. 60/043,986, Apr. 3, 1997.

[51] Int. Cl.$^7$ .................................................. C07C 37/00
[52] U.S. Cl. ............................................................ 568/800
[58] Field of Search ............................................. 568/800

[56] References Cited

U.S. PATENT DOCUMENTS

| | | | |
|---|---|---|---|
| 3,702,886 | 11/1972 | Argauer et al. | 423/328 |
| 3,945,943 | 3/1976 | Ward | 252/455 |
| 4,258,222 | 3/1981 | Möhring et al. | 568/863 |
| 4,579,993 | 4/1986 | Bowes et al. | 585/640 |
| 4,982,013 | 1/1991 | Gubelmann et al. | 568/771 |
| 5,001,280 | 3/1991 | Gubelmann et al. | 568/716 |
| 5,019,657 | 5/1991 | Gubelmann et al. | 568/774 |
| 5,055,623 | 10/1991 | Gubelmann et al. | 568/800 |
| 5,110,995 | 5/1992 | Kharitonov et al. | 568/800 |
| 5,171,553 | 12/1992 | Li et al. | 423/239 |
| 5,502,259 | 3/1996 | Zakoshansky et al. | 568/754 |
| 5,534,135 | 7/1996 | Dai et al. | 208/120 |
| 5,892,132 | 4/1999 | Rooks | 568/771 |

FOREIGN PATENT DOCUMENTS

| | | |
|---|---|---|
| 0 421 422 A2 | 4/1991 | European Pat. Off. |
| 2 010 790 | 4/1994 | Russian Federation |
| 2 116 974 | 3/1993 | United Kingdom |
| WO 93/02994 | 2/1993 | WIPO |
| 95/27560 | 10/1995 | WIPO |
| 95/27691 | 10/1995 | WIPO |
| WO 97/04871 | 2/1997 | WIPO |

OTHER PUBLICATIONS

Li et al. (1992) *Catalytic Decomposition Of Nitrous Oxide On Metal Exchanged Zeolites;* Applied Catalysis B: Environmental 1, L21–29; Elsevier Science Publishers B.V., Amsterdam.

Sobolev et al. (1993) *Catalytic Properties Of ZSM–5 Zeolites In $N_2O$ Decomposition: The Role Of Iron;* Journal of Catalysis 139, 435–443; Academic Press, Inc.

Sobolev et al. (1993) *Stoichiometric Reaction Of Benzene With $\alpha$–Form Of Oxygen On Fezsm–5 Zeolites. Mechanism Of Aromatics Hydroxylation By $N_2O$;* Journal of Molecular Catalysis 84, 117–124; Elsevier Science Publishers B.V., Amsterdam.

Panov et al. (1992) *Oxidation Of Benzene To Phenol By Nitrous Oxide Over Fe–ZSM–5 Zeolites;* Applied Catalysis A: General 82, 31–36, Elsevier Science Publishers B.V., Amsterdam.

Kharitonov et al. (1993) *Ferrisilicate Analogs Of ZSM–5 Zeolite As Catalysts For One Step Oxidation Of Benzene To Phenol,* Applied Catalysis A: General 98, 33–43, Elsevier Science Publishers B.V., Amsterdam.

Burch et al. (1993) *Factors Affecting The Deactivation Of Various Zeolites Used As Catalysts For The Direct Partial Oxidation Of Benzene To Phenol Applied Catalysis A:* General 106, 167–183, Elsevier Science Publishers B.V., Amsterdam.

Burch et al. (1993) *Investigation Of Zeolite Catalysts For The Direct Partial Oxidation Of Benzene To Phenol;* Applied Catalysis A: General 103, 135–162, Elsevier Science Publishers B.V., Amsterdam.

Burch et al. (1993) *Direct Partial Oxidation Of Benzene To Phenol On Zeolite Catalysts;* Applied Catalysis A: General 86, 139–146, Elsevier Science Publishers B.V., Amsterdam.

Panov et al. (1993) *Oxidative Hydroxylation Using Dinitrogen Monoxide; A Possible Route For Organic Synthesis Over Zeolites,* Applied Catalysis A: General, 98, 1–20, Elsevier Science Publishers B.V., Amsterdam.

Derwent abstract; JP 5 009 142 (1993).
Derwent abstract, JP 4 334 333 (1992).
Derwent abstract, JP 4 021 645 (1996).
Derwent abstract, JP 6 009 464 (1998).
Derwent abstract, JP 6 040 976 (1998).

(List continued on next page.)

*Primary Examiner*—Michael L Shippen

[57] ABSTRACT

A process for hydroxylating an aromatic compound comprises the steps of: (a) contacting an aromatic compound with a catalyst having an average concentration of $\alpha$-sites of at least about $1 \cdot 10^{16}$ per gram of catalyst, the catalyst having $\alpha$-oxygen loaded thereon, whereby an hydroxylated derivative of the aromatic compound is produced; and (b) regenerating the catalyst when the concentration of $\alpha$-sites falls below a predetermined value. The predetermined value will depend on the process design, but can suitably be about $1 \cdot 10^{16}$ per gram of catalyst or higher.

Another embodiment of the process comprises: (a) contacting an aromatic compound with a catalyst having an average concentration of $\alpha$-sites of at least about $1 \cdot 10^{16}$ per gram of catalyst, the catalyst having $\alpha$-oxygen loaded thereon, whereby an hydroxylated derivative of the aromatic compound is produced; and (b) reloading the catalyst with $\alpha$-oxygen by contacting the catalyst with a free oxidant activator. The progress of the reloading of the catalyst can be determined by: (a) passing an input gas stream over the catalyst, the input gas stream comprising an inert gas; (b) collecting an output gas stream that has passed over the catalyst; (c) introducing a plurality of nitrous oxide impulses into the input gas stream, each impulse being separated by a period in which the input gas stream contains no nitrous oxide; (d) measuring the concentrations of nitrous oxide and nitrogen gas in the output gas stream after an impulse of nitrous oxide is introduced; and (e) comparing the concentrations of nitrogen gas and nitrous oxide in the output gas stream.

25 Claims, 3 Drawing Sheets

OTHER PUBLICATIONS

Derwent abstract, EP 406 050 (1991).

Dvorak et al. (1970) *Determination Of The Specific Copper Surface Area By Chromatographic Technique*; Journal of Catalysis 18, 108–114, Academic Press, Inc.

Evans et al. (1983) *On The Determination Of Copper Surface Area By Reaction With Nitrous Oxide;* Applied Catalysis 7, 75–83, Elsevier Science Publishers B.V.

Iwamoto et al. (1983) *Catalytic Oxidation By Oxide Radical Ions. 1. One–Step Hydroxylation Of Benzene To Phenol Over Group 5 And 6 Oxides Supported On Silica Gel;* The Journal of Physical Chemistry 87, No. 6, The American Chemical Society.

Ono et al. (1988) *Functionalization Of Benzene By Its Reaction With Nitrogen Oxides Over Solid–Acid Catalysts,* Heterogeneous Catalysis and Fine Chemicals pp. 75–82, Elsevier Science Publishers BV., Amsterdam.

Suzuki et al. (1988) *Hydroxylation Of Benzene With Dinitrogen Monoxide Over H–ZSM–5 Zeolite,* Chemistry Letters pp. 953,956, The Chemical Society of Japan.

Panov et al. (1990) *The Role Of Iron In $N_2O$ Decomposition On ZSM–5 Zeolite And Reactivity Of The Surface Oxygen Formed,* Journal of Molecular Catalysis 61, 85–97, Elsevier Sequoia.

Sobolev et al. (1991) *Anomalously Low Bond Energy Of Surface Oxygen On FeZSM–5 Zeolite,* Mendeleev Communications, No. 1, pp. 29–30.

Zholobenko (1993) *Preparation Of Phenol Over Dehydroxylated HZSM–5 Zeolites* Mendeleev–Communications, pp. 23–24.

Hafele et al. (1996) *Hydroxylation of Benzene on ZSM5 Type Catalysis,* DGMK–Conference, Catalysis On Solid Acids And Bases pp. 243–251.

Vereschagin et al., *Conversion Of Ethane On Zeolite Catalysts In The Presence Of Oxygen And Nitrogen*(I) Ox De, Izv. Akad Nauk SSSR, (1988), 1718–1722 (English abstract translated from a Russian article).

Wen–Qing Xu et al., "Modification of Non–template Synthesized Ferrierite/ZSM–35 for n–Butene Skeletal Isomerization to Isobutylene," Journal of Catalysts, vol. 163, pp. 232–244 (1996).

Tsutsumi et al, "Adsorption Characteristics of Hydrophobic Zeolites," Proceedings of the International Symposium on Zeolites and Microporous Crystals, Nagoya, vol. 83, pp. 217–224 (Aug. 22–25, 1993).

Effects of ZSM-5 (ANG) steaming temperature

Effects of ZSM-5 (ANG) steaming temperature

PROCESS FOR MAKING PHENOL OR PHENOL DERIVATIVES

This application claims the benefit of provisional application Ser. No. 60/043,986, filed on Apr. 3, 1997.

BACKGROUND OF THE INVENTION

The present invention relates to a process for converting aromatic compounds such as benzene or derivatives thereof to their hydroxylated derivatives, such as phenol or related compounds.

It is known that phenol or a derivative thereof can be produced by a single-step oxidative hydroxylation of benzene or a derivative thereof, using nitrous oxide over a catalyst. For example, PCT publication WO 95/27560 describes such a process that employs a zeolite catalyst whose performance is enhanced by hydrothermal treatment. However, in the past, the characteristics needed in a catalyst in order for this reaction to proceed efficiently have not been completely understood.

Therefore, a need exists for improved catalysts and processes for conversion of aromatic hydrocarbons such as benzene to their hydroxylated derivatives, in which cost is minimized while yield and selectivity are maximized.

SUMMARY OF THE INVENTION

One aspect of the present invention is a process for hydroxylating an aromatic compound. The process includes the steps of: (a) contacting an aromatic compound with a catalyst having an average concentration of α-sites of at least about $1 \cdot 10^{16}$ per gram of catalyst, the catalyst having α-oxygen loaded thereon, whereby an hydroxylated derivative of the aromatic compound is produced; and (b) regenerating the catalyst when the concentration of α-sites falls below a predetermined value. The predetermined value will depend on the process design, but can suitably be about $1 \cdot 10^{16}$ per gram of catalyst. The predetermined value in one preferred embodiment is at least about $5 \cdot 10^{16}$ per gram of catalyst, more preferably at least about $1 \cdot 10^{16}$ per gram of catalyst, even more preferably at least about $1 \cdot 10^{18}$ per gram of catalyst.

In another embodiment, the process comprises: (a) contacting an aromatic compound with a catalyst having an average concentration of α-sites of at least about $1 \cdot 10^{16}$ per gram of catalyst, the catalyst having α-oxygen loaded thereon, whereby an hydroxylated derivative of the aromatic compound is produced; and (b) reloading the catalyst with α-oxygen by contacting the catalyst with a free oxidant activator. The progress of the reloading of the catalyst can be determined by: (a) passing an input gas stream over the catalyst, the input gas stream comprising an inert gas; (b) collecting an output gas stream that has passed over the catalyst; (c) introducing a plurality of impulses of a free oxidant activator, such as nitrous oxide, into the input gas stream, each impulse being separated by a period in which the input gas stream contains no nitrous oxide; (d) measuring the concentrations of nitrous oxide and nitrogen gas in the output gas stream after an impulse of nitrous oxide is introduced; and (e) comparing the concentrations of nitrogen gas and nitrous oxide in the output gas stream. The concentrations of nitrous oxide and nitrogen gas in the output gas stream can be determined by chromatography, among other methods.

The aromatic compound preferably is contacted with the catalyst at a temperature between about 100–500° C., with the aromatic compound preferably in the form of a gas, and mixed with an inert diluent gas. When the aromatic reactant is benzene and the product is phenol, a temperature of about 300–350° C. is preferred. It is also preferred that prior to the hydroxylation reaction, the catalyst has been hydrothermally treated by contacting it with steam. The aromatic compound alternatively could be in liquid form when contacted with the catalyst.

One preferred free oxidant activator for loading and reloading the catalyst with α-oxygen is nitrous oxide. The loading/reloading is done at a temperature between about 100–600° C., most preferably between about 100–300° C.

In one embodiment of the invention, the time for commencing reloading of the catalyst with α-oxygen can be determined by: (a) passing an input gas stream over the catalyst, the input gas stream comprising an inert gas; (b) collecting an output gas stream that has passed over the catalyst; (c) introducing a plurality of nitrous oxide impulses into the input gas stream, each impulse being separated by a period in which the input gas stream contains no nitrous oxide; (d) measuring the concentrations of nitrous oxide and nitrogen gas in the output gas stream after an impulse of nitrous oxide is introduced; and (e) comparing the concentrations of nitrogen gas and nitrous oxide in the output gas stream. A ratio of nitrogen gas to nitrous oxide in the output gas stream that is at or above a predetermined value, for example 1:1 or greater, is deemed an indication that the catalyst needs to be reloaded with α-oxygen.

Once the reloading of the catalyst with α-oxygen is commenced, the progress of the reloading can be monitored by the same type of pulse method, such as: (a) passing an input gas stream over the catalyst, the input gas stream comprising an inert gas; (b) collecting an output gas stream that has passed over the catalyst; (c) introducing a plurality of nitrous oxide impulses into the input gas stream, each impulse being separated by a period in which the input gas stream contains no nitrous oxide; (d) measuring the concentration of nitrous oxide and nitrogen gas in the output gas stream; and (d) determining when the ratio of nitrous oxide to nitrogen gas in the output gas stream reaches a predetermined value, such as at least about 5:1, such a ratio being deemed an indication that the catalyst has been sufficiently reloaded. In a preferred embodiment, the reloading is continued until the ratio in the output gas stream is at least about 100:1.

Another aspect of the present invention is a method of preparing a catalyst for hydroxylation of an aromatic compound. The method includes loading a zeolite catalyst with α-oxygen by contacting the catalyst with an input gas stream that comprises an inert gas and a free oxidant activator, where the catalyst has an average concentration of α-sites that is above a predetermined value, for example at least about $1 \cdot 10^{16}$ per gram of catalyst. As mentioned above, in certain preferred embodiments, the predetermined value is at least about $5 \cdot 10^{16}$ per gram of catalyst, more preferably at least about $1 \cdot 10^{17}$ per gram of catalyst, even more preferably at least about $1 \cdot 10^{18}$ per gram of catalyst. As also mentioned above, the preparation of the catalyst preferably includes hydrothermal treatment. Preparation of the catalyst can be monitored with a pulse method as described above, in which the ratio of nitrous oxide to nitrogen gas in the output gas stream is determined.

In one embodiment, the process of the present invention involves the following general reaction.

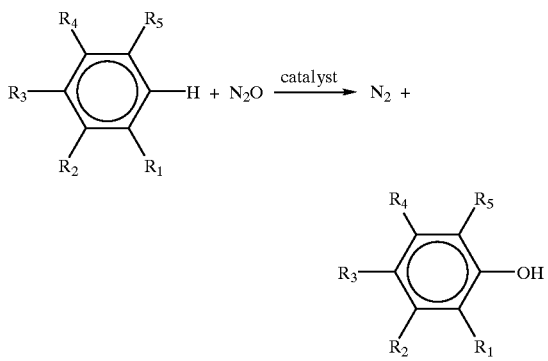

$R_1$, $R_2$, $R_3$, $R_4$, and $R_5$ can be independently selected from the group consisting of hydrogen, hydroxyl, halogen, aliphatic hydrocarbons having 1–20 carbon atoms, carboxyl, amino, nitro, and thio groups. In one preferred embodiment, one of $R_1$–$R_5$ is selected from the group consisting of hydrogen, hydroxyl, halogen, and alkyl groups having 1–4 carbon atoms, and the rest of $R_1$–$R_5$ are hydrogen.

The present invention has a number of advantages over prior art processes. It provides a simple and economical method for making phenol and derivatives thereof. Further, it provides a simple and relatively inexpensive way of monitoring and controlling the preparation of the catalyst, by determining the concentration of α-sites in the catalyst. The process also exhibits high selectivity for the desired hydroxylated product.

DESCRIPTION OF ILLUSTRATIVE EMBODIMENTS

Figure 1A:
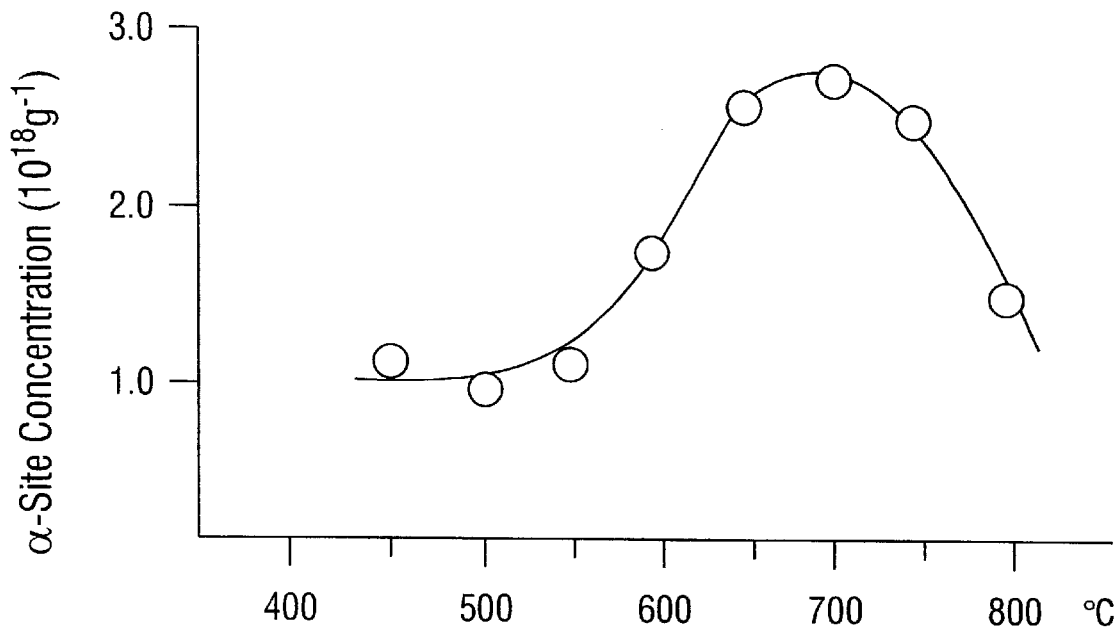
FIG. 1 is a graph showing the effect of steaming temperature for a ZSM-5 catalyst on (1) α-site concentration, (2) channel hollowness, (3) stability in the conversion of benzene to phenol, and (4) activity in the conversion of benzene to phenol.
Figure 1B:
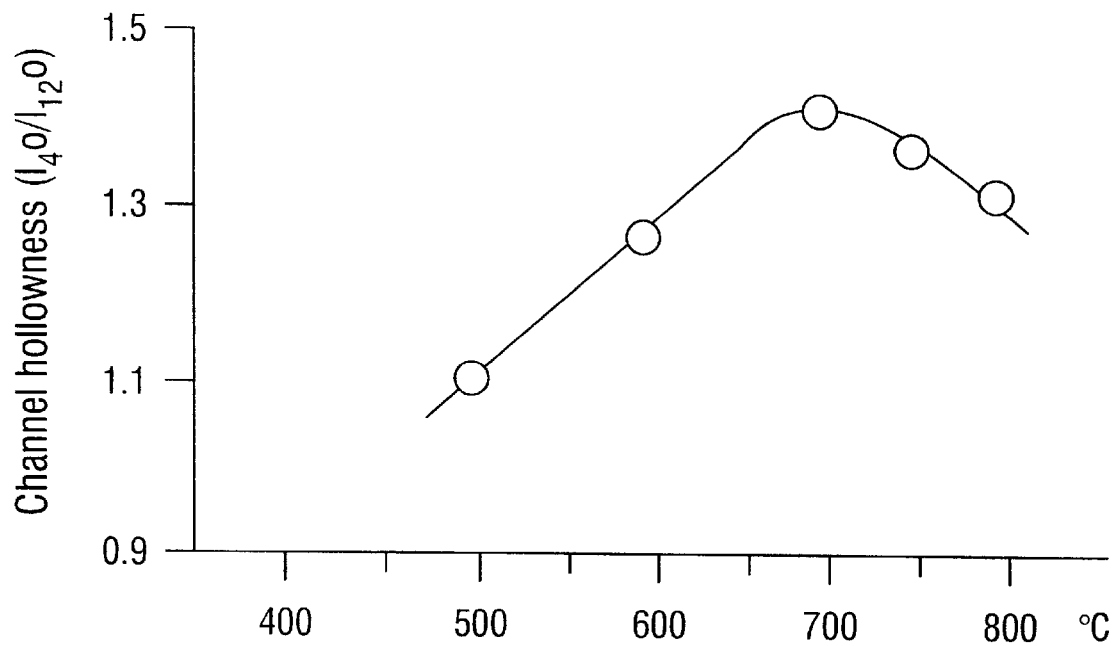
Figure 1C:
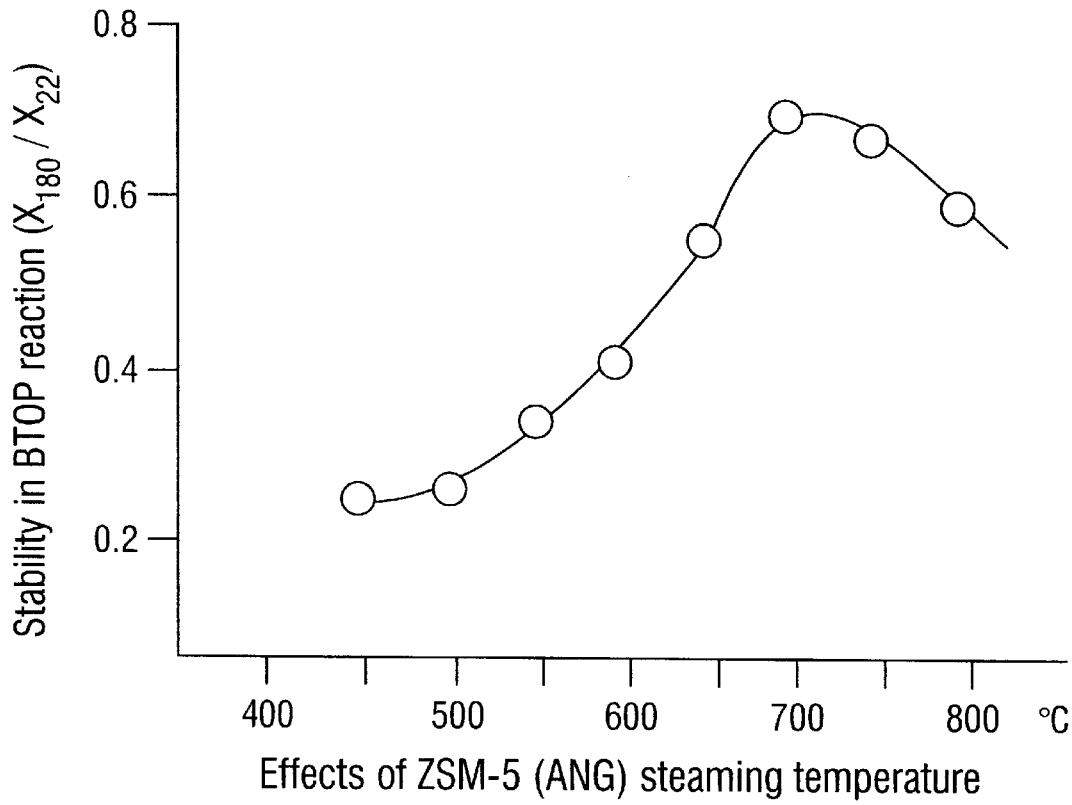
Figure 1D:
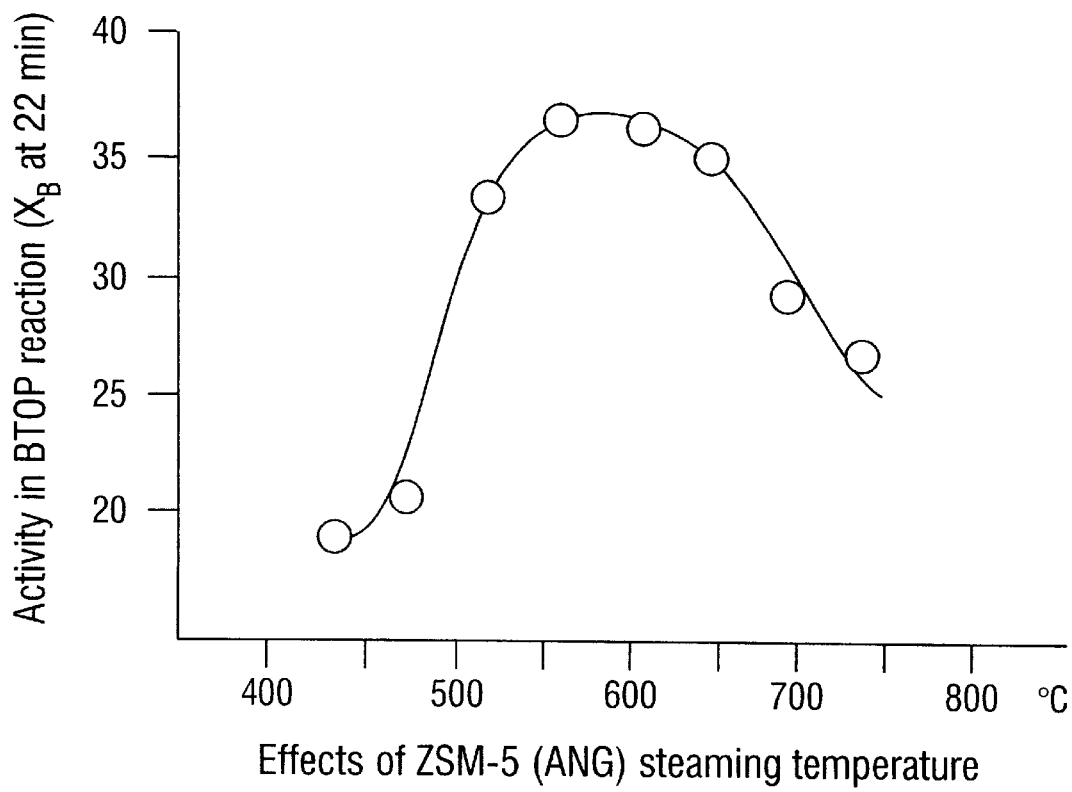

Aromatic compounds can be hydroxylated in the process of the present invention. Preferred aromatic compounds have from about 6–20 carbon atoms. The aromatic reactant can be substituted with one or more substituents such as halogens, aliphatic hydrocarbons having from 1–20 carbon atoms, hydroxyl, carboxyl, amino, nitro, or thio groups, provided however that at least one carbon on the aromatic ring must have a carbon-hydrogen bond. The present invention is especially useful in the hydroxylation of benzene and benzene derivatives such as chlorobenzene, fluorobenzene, toluene, ethylbenzene, and the like, into phenols or the corresponding substituted phenol. If phenol itself is the benzene derivative used as the reactant, the reaction products can include polyols such as hydroquinone, resorcinol, and catechol.

Suitable solid-phase catalysts for use in the present invention include zeolites. Zeolites having the MFI and MEL structural types are preferred, and ZSM-5 and ZSM-11 catalysts are especially preferred. Such zeolites are commercially available from vendors such as Zeolyst International, UOP, Mobil, and others. FeZSM-5 zeolites are especially preferred. An Fe content of about 0.05–1.0 weight % is desirable.

Catalysts for use in the hydroxylation reaction contain a minimum concentration of α-sites, specific surface centers that are able to produce a special active form of oxygen (α-oxygen) under decomposition of a free oxidant activator. A preferred free oxidant activator is $N_2O$. Other suitable free oxidant activators include ozone and peroxides such as hydrogen peroxide. At temperatures below about 300° C., $N_2O$ decomposes over α-sites on a catalyst according to the reaction:

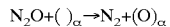

The presence of α-oxygen in these sites enables the hydroxylation of the aromatic ring.

The hydroxylation reaction is carried out by contacting the aromatic substrate, preferably as a gas, with the α-oxygen-bearing catalyst. The loading of the catalyst with α-oxygen (i.e., the decomposition of the free oxidant activator) and the hydroxylation of the aromatic compound can be done simultaneously in the same reactor, or can be separated (i.e., physically separated in two separate reactors or in two separate zones of a single reactor, or temporally separated as sequential activities in a single reactor).

Prior to the hydroxylation reaction, the catalyst is preferably hydrothermally treated with steam. The steam treatment significantly enhances the activity of the catalyst in the hydroxylation reaction, although it does not change the chemical composition of the catalyst, or the catalyst's surface area, micropore volume, or crystal structure. Key parameters for the steam treatment step are steam concentration, temperature, and duration of the treatment. Preferred values are steam concentration between about 3–100 mole percent of the overall gas phase during the hydrothermal treatment step, temperature between about 350–950° C., and duration of treatment between about 0.1–24 hours.

Table 1 and FIG. 1 show the effect of steaming temperature on concentration of α-sites and catalytic activity of a ZSM-5 zeolite. In the experiments summarized in the table, the catalyst was treated with a gas phase containing 50 mole % $H_2O$ and the remainder He for two hours. $X_0$ refers to conversion and $S_0$ refers to benzene selectivity for phenol.

TABLE 1

| Experiment | Treatment temperature (° C.) | $C_\alpha$(site/g) | $X_0$ (%) | $S_0$ (%) |
|---|---|---|---|---|
| 1 | no treatment | $5.0 \cdot 10^{17}$ | 8.5 | 92.5 |
| 2 | 450 | $1.2 \cdot 10^{18}$ | 19.0 | 93.0 |
| 3 | 500 | $1.0 \cdot 10^{18}$ | 18.5 | 93.5 |
| 4 | 550 | $1.1 \cdot 10^{18}$ | 33.5 | 93.0 |
| 5 | 600 | $1.8 \cdot 10^{18}$ | 37.0 | 95.0 |
| 6 | 650 | $2.6 \cdot 10^{18}$ | 36.5 | 93.5 |
| 7 | 700 | $2.8 \cdot 10^{18}$ | 31.5 | 95.5 |
| 8 | 750 | $2.6 \cdot 10^{18}$ | 27.5 | 96.0 |
| 9 | 800 | $1.5 \cdot 10^{18}$ | 26.8 | 93.2 |

This shows that the concentration of α-sites in the catalyst ($C_\alpha$) is a good indicator of the functional properties of the catalyst in the hydroxylation of an aromatic compound such as benzene. Thus $C_\alpha$ can be used both for control of the steam activation step and for final control over the catalyst preparation technology as a whole.

It should also be noted that the apparent concentration of α-sites in a catalyst will be affected by the extent of coking that has taken place. A catalyst that starts out with a given $C_\alpha$ will experience coking as it is used in the hydroxylation reaction, causing $C_\alpha$ to decrease over time. Therefore, measurement of $C_\alpha$ can also be used as an indication of when the catalyst needs to be regenerated (i.e., decoked).

Figure 2:
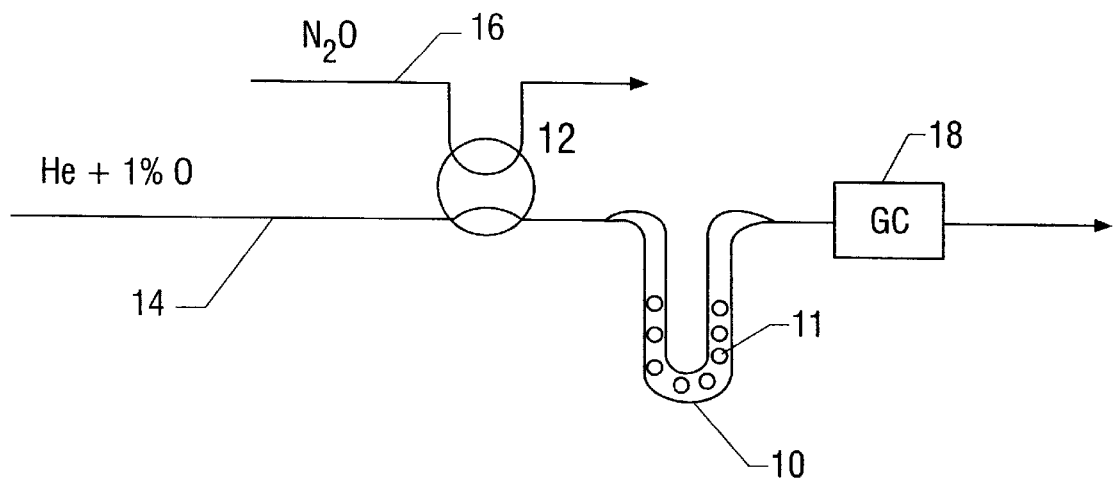
FIG. 2 is a schematic diagram of a pulse-chromatographic system for measurement of α-site concentration of a catalyst.

$C_\alpha$ of the catalyst can be determined by any of several means, such as (1) a vacuum static system with mass spectrometric analysis of the gas phase, (2) isotope exchange with $^{18}O$, or (3) stoichiometric reaction of the aromatic substrate with the α-oxygen-bearing catalyst, with $C_\alpha$ being determined with by consumption of the aromatic reactant or by extraction of the hydroxylated product. However, it is preferred to determine $C_\alpha$ by using a flow impulse system with chromatographic analysis of the gas phase, as shown in FIG. 2. The system of FIG. 2 includes a reactor 10 containing a suitable catalyst 11, and an injection valve 12. A feed line 14 carries a gas stream comprising primarily inert gas through the valve 12 and into the reactor 10. A second feed line 16 carries a gas stream of $N_2O$ to the valve 12. A gas chromatograph 18 is located on the conduit exiting the reactor 10.

After the catalyst sample 11 is loaded into the reactor 10, a flow of He containing 0.05–10.0 mol % $O_2$ is started through the reactor. This flow continues uninterrupted until the end of the test. The reactor is heated to 400–550° C. for 1–2 hours. The reactor is then cooled to 100–300° C. $C_\alpha$ is determined at this temperature, by introducing impulses of $N_2O$ into the reactor (using the valve 12) intermittently, each pulse of $N_2O$ having a known volume. The gas chromatograph 18 is used to measure the concentrations of $N_2O$ and $N_2$ in the reactor output.

Figure 3:
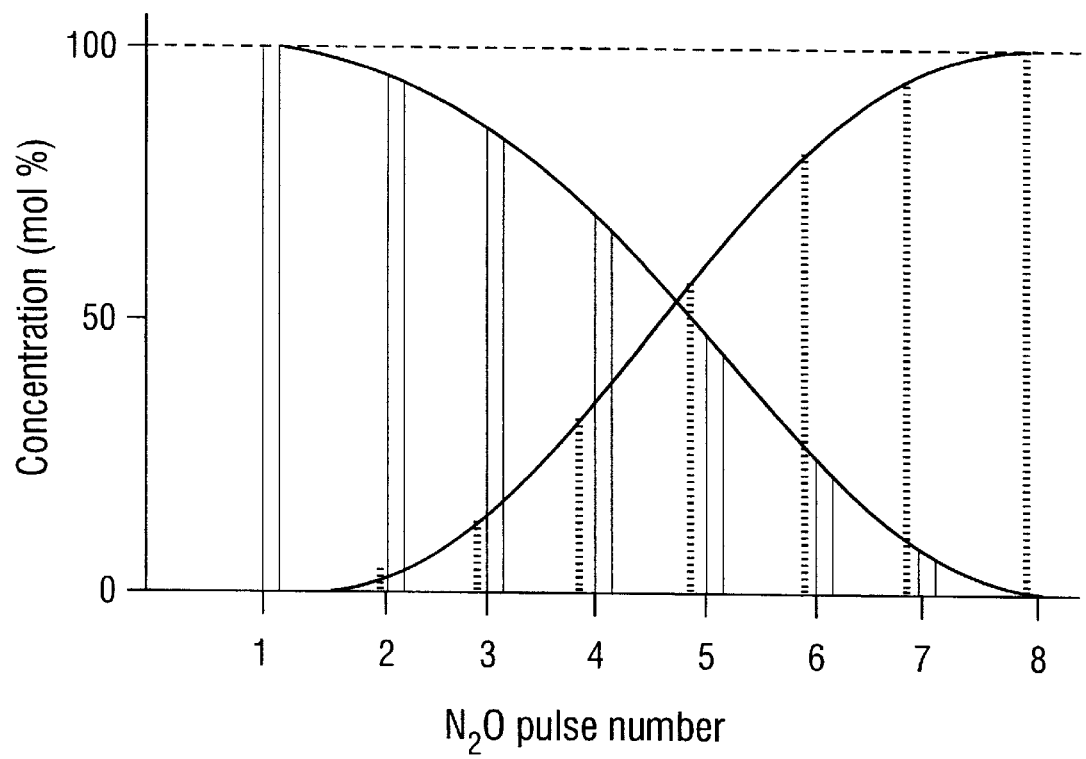
FIG. 3 is a graph showing the concentrations of $N_2O$ and $N_2$ as a function of $N_2O$ pulse number in the system of FIG. 2.

FIG. 3 shows the change in $N_2O$ and $N_2$ concentration in the reactor output as a function of pulse number. Essentially complete decomposition of $N_2O$ is observed in the first pulse. Thereafter, $N_2O$ decomposition diminishes and, as α-sites are filled by oxygen, eventually stops. In other words, as the number of cumulative $N_2O$ pulses increases, the concentration of $N_2O$ in the reactor output after each successive pulse increases and the concentration of $N_2$ in the output decreases. $C_\alpha$ can be determined according to the stoichiometry of the reaction. For example, the area of the nitrogen chromatographic peak or the difference between the areas of inlet and outlet of nitrous oxide peaks can be used for calculation of amount of $N_2O$ decomposed and thus α-site concentration.

A sample calculation of $C_\alpha$ is as follows. If the catalyst weight is 1 g, the reaction volume (e.g., a calibrated loop) in the reactor is 1 $cm^3$, and the $N_2O$ concentration in the loop is 5 %, then the amount of $N_2O$ in one pulse is equal to 0.00223 mmol (1 $cm^3$·0.05/22.4 $cm^3$/mmol). Table 2 shows the "theoretical" change of $N_2O$ and $N_2$ concentration ($C(N_2O)$ and $C(N_2)$) in the output gas and the amount of $N_2O$ decomposed ($A(N_2O)$) versus pulse number.

TABLE 2

| Pulse | $C(N_2O)$, % | $C(N_2)$, % | $A(N_2O)$, mmol |
|---|---|---|---|
| 1 | 0 | 5 | 0.00223 |
| 2 | 0 | 5 | 0.00223 |
| 3 | 2 | 3 | 0.00134 |
| 4 | 4 | 1 | 0.00045 |
| 5 | 5 | 0 | 0 |

The overall amount of $N_2O$ decomposed in the five pulses is 0.00625 mmol. On the assumption that $N_2O$ decomposition proceeds according to reaction:

$N_2O + ( )_\alpha = N_2 + (O)_\alpha$ where one active site is connected with one oxygen atom from $N_2O$, the α-site concentration ($C_\alpha$) can be calculated from the amount of $N_2O$ decomposed. In this example, $C_\alpha$ is equal to $3.8 \cdot 10^{18}$ sites/g (0.00625 mmol·$6 \cdot 10^{20}$ molec./mmol/1 g).

Some catalysts, processes, and equipment that can be used in the present invention are disclosed in one or more of U.S. application Ser. No. 08/693,432, filed on Aug. 7, 1996; U.S. Ser. No. 08/695,239, filed on Aug. 8, 1996; U.S. Ser. No. 08/700,142, filed on Aug. 20, 1996; and U.S. Ser. No. 08/700,146, filed on Aug. 20, 1996, each of which is incorporated here by reference.

The preceding description of specific embodiments of the present invention is not intended to be a complete list of every possible embodiment of the invention. Persons skilled in this field will recognize that modifications can be made to the specific embodiments described here that would be within the scope of the present invention.

What is claimed is:

1. A process for hydroxylating an aromatic compound, comprising:

contacting an aromatic compound with a catalyst having an average concentration of α-sites of at least about $1 \cdot 10^{16}$ per gram of catalyst, the catalyst having α-oxygen loaded thereon, whereby an hydroxylated derivative of the aromatic compound is produced;

reloading the catalyst with α-oxygen by contacting the catalyst with a free oxidant activator; and determining the progress of the reloading by:

passing an input gas stream over the catalyst, the input gas stream comprising an inert gas;

collecting an output gas stream that has passed over the catalyst;

introducing a plurality of nitrous oxide impulses into the input gas stream, each impulse being separated by a period in which the input gas stream contains no nitrous oxide;

measuring the concentrations of nitrous oxide and nitrogen gas in the output gas stream after an impulse of nitrous oxide is introduced; and comparing the concentrations of nitrogen gas and nitrous oxide in the output gas stream.

2. The process of claim 1, where the free oxidant activator is nitrous oxide.

3. The process of claim 1, where the catalyst has an average concentration of α-sites of at least about $5 \cdot 10^{16}$ per gram of catalyst.

4. The process of claim 1, where the catalyst has an average concentration of α-sites of at least about $1 \cdot 10^{17}$ per gram of catalyst.

5. The process of claim 1, where the catalyst has an average concentration of α-sites of at least about $1 \cdot 10^{18}$ per gram of catalyst.

6. The process of claim 1, where the aromatic compound has the formula:

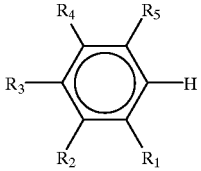

where $R_1$, $R_2$, $R_3$, $R_4$, and $R_5$ are selected independently from the group consisting of hydrogen, hydroxyl, halogen, aliphatic hydrocarbons having 1–20 carbon atoms, carboxyl, amino, nitro, and thio groups.

7. The process of claim 1, where the aromatic compound has the formula:

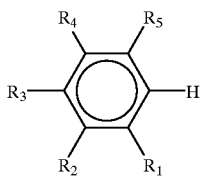

where one of $R_1$, $R_2$, $R_3$, $R_4$, and $R_5$ is selected from the group consisting of hydrogen, hydroxyl, halogen, and alkyl groups having 1–4 carbon atoms, and the rest of $R_1$, $R_2$, $R_3$, $R_4$, and $R_5$ are hydrogen.

8. The process of claim 1, where the aromatic compound is a gas when contacted with the catalyst.

9. The process of claim 1, further comprising:
regenerating the catalyst when the concentration of α-sites therein falls below about $1 \cdot 10^{16}$ per gram of catalyst.

10. The process of claim 9, where the catalyst is regenerated when the concentration of α-sites therein falls below about $5 \cdot 10^{16}$ per gram of catalyst.

11. The process of claim 9, where the catalyst is regenerated when the concentration of α-sites therein falls below about $1 \cdot 10^{17}$ per gram of catalyst.

12. The process of claim 9, where the catalyst is regenerated when the concentration of α-sites therein falls below about $1 \cdot 10^{18}$ per gram of catalyst.

13. The process of claim 1, where the concentrations of nitrous oxide and nitrogen gas in the output gas stream are determined by chromatography.

14. The process of claim 1, where the time for commencing reloading of the catalyst with α-oxygen is determined by:
passing an input gas stream over the catalyst, the input gas stream comprising an inert gas;
collecting an output gas stream that has passed over the catalyst;
introducing a plurality of nitrous oxide impulses into the input gas stream, each impulse being separated by a period in which the input gas stream contains no nitrous oxide;
measuring the concentrations of nitrous oxide and nitrogen gas in the output gas stream after an impulse of nitrous oxide is introduced; and
comparing the concentrations of nitrogen gas and nitrous oxide in the output gas stream; and
determining when the ratio of nitrogen gas to nitrous oxide in the output gas stream exceeds a predetermined value.

15. The process of claim 14 where a ratio of nitrogen gas to nitrous oxide in the output gas stream of 1:1 or greater is deemed an indication that the catalyst needs to be reloaded with α-oxygen.

16. The process of claim 1, where the reloading is done at a temperature between about 100–600° C.

17. The process of claim 1, where the reloading is done at a temperature between about 100–300° C.

18. The process of claim 1, where the reloading of the catalyst is monitored by:
passing an input gas stream over the catalyst, the input gas stream comprising an inert gas;
collecting an output gas stream that has passed over the catalyst;
introducing a plurality of nitrous oxide impulses into the input gas stream, each impulse being separated by a period in which the input gas stream contains no nitrous oxide;
measuring the concentration of nitrous oxide and nitrogen gas in the output gas stream; and
determining when the ratio of nitrous oxide to nitrogen gas in the output gas stream exceeds a predetermined ratio.

19. The process of claim 18, where ratio of nitrous oxide to nitrogen gas in the output gas stream of at least 5:1 is deemed an indication that the catalyst has been sufficiently reloaded.

20. The process of claim 18, where ratio of nitrous oxide to nitrogen gas in the output gas stream of at least 100:1 is deemed an indication that the catalyst has been sufficiently reloaded.

21. The process of claim 1, where the aromatic compound is benzene and the hydroxylated derivative is phenol.

22. The process of claim 1, where the aromatic compound is contacted with the catalyst at a temperature between about 100–500° C.

23. The process of claim 1, where the aromatic compound is contacted with the catalyst in the presence of an inert diluent gas.

24. The process of claim 1, where the catalyst has been hydrothermally treated by contacting it with a gas comprising approximately 1–100 mole percent water at a temperature between about 350–950° C.

25. The process of claim 1, where the catalyst is a zeolite.

* * * * *

UNITED STATES PATENT AND TRADEMARK OFFICE
CERTIFICATE OF CORRECTION

PATENT NO. : 6,156,938
DATED : December 5, 2000
INVENTOR(S) : Sobolev, et al.

It is certified that error appears in the above-identified patent and that said Letters Patent is hereby corrected as shown below:

Column 1,
Line 40, please delete "$1-10^{16}$" and insert -- $1-10^{17}$ --

Signed and Sealed this

Twenty-fifth Day of September, 2001

Attest:

NICHOLAS P. GODICI
Attesting Officer     Acting Director of the United States Patent and Trademark Office